United States Patent
Nakamura et al.

(10) Patent No.: US 7,556,771 B2
(45) Date of Patent: Jul. 7, 2009

(54) AUTOMATIC ANALYZING SYSTEM

(75) Inventors: Kazuhiro Nakamura, Naka (JP); Toshihide Orihashi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 575 days.

(21) Appl. No.: 10/606,835

(22) Filed: Jun. 27, 2003

(65) Prior Publication Data

US 2004/0091396 A1    May 13, 2004

(30) Foreign Application Priority Data

Jun. 28, 2002    (JP) .............................. 2002-189014

(51) Int. Cl.
    *G01N 21/00* (2006.01)
(52) U.S. Cl. .............................. 422/67; 63/65; 63/67.1; 63/68.1; 700/106
(58) Field of Classification Search ................... 422/63, 422/65, 67, 68.1, 67.1; 700/106
    See application file for complete search history.

(56) References Cited

U.S. PATENT DOCUMENTS

| | | | | |
|---|---|---|---|---|
| 4,731,225 A | * | 3/1988 | Wakatake | 422/65 |
| 5,679,309 A | * | 10/1997 | Bell | 422/67 |
| 5,746,977 A | * | 5/1998 | Imai et al. | 422/62 |
| 5,902,549 A | * | 5/1999 | Mimura et al. | 422/65 |
| 6,080,364 A | * | 6/2000 | Mimura et al. | 422/67 |
| 6,090,630 A | * | 7/2000 | Koakutsu et al. | 436/50 |
| 6,261,521 B1 | * | 7/2001 | Mimura et al. | 422/67 |
| 6,723,288 B2 | * | 4/2004 | Devlin et al. | 422/65 |
| 6,733,728 B1 | * | 5/2004 | Mimura et al. | 422/65 |
| 6,924,152 B2 | * | 8/2005 | Matsubara et al. | 436/180 |
| 7,011,792 B2 | * | 3/2006 | Mimura et al. | 422/67 |
| 7,029,922 B2 | * | 4/2006 | Miller | 436/180 |
| 7,097,808 B1 | * | 8/2006 | Onuma | 422/63 |
| 2005/0013736 A1 | * | 1/2005 | McKeever | 422/63 |
| 2005/0013737 A1 | * | 1/2005 | Chow et al. | 422/63 |
| 2006/0051243 A1 | * | 3/2006 | Chow et al. | 422/82.08 |
| 2006/0110288 A1 | * | 5/2006 | Mimura et al. | 422/63 |
| 2006/0148063 A1 | * | 7/2006 | Fauzzi et al. | 435/286.4 |

FOREIGN PATENT DOCUMENTS

JP    9-243646    9/1997

* cited by examiner

*Primary Examiner*—Brian R. Gordon
(74) *Attorney, Agent, or Firm*—Mattingly & Malur, P.C.

(57) ABSTRACT

A reagent shortage detection unit detects that one of the reagents of reagent supply units of analyzing apparatuses is shortage. A reagent shortage occurrence display unit notifies the shortage of the one reagent in response to that the reagent shortage detection unit detects that the one reagent of the analyzing apparatuses is shortage. A control separation unit separates from the control of the analyzing system, the analyzing apparatus in which the one reagent is shortage, in accordance with reagent shortage detection information from the reagent shortage detection unit.

7 Claims, 5 Drawing Sheets

AUTOMATIC ANALYZING SYSTEM

BACKGROUND OF THE INVENTION

1. Field of the Invention

The present invention relates to an automatic analyzing system including an automatic analyzing apparatus for automatically analyzing a living body sample such as blood or urine and, in particular, relates to an automatic analyzing system in which plural automatic analyzing apparatuses are coupled and a sample is mounted at each of the analyzing apparatuses.

2. Description of the Related Art

Conventionally, in an automatic analyzing apparatus for analyzing samples of living bodies such as blood or urine, the analysis is made by using so-called stand-alone apparatuses in which the respective apparatuses perform the analysis independently. However, in recent years, an automatic analyzing system is proposed in which, in order to improve the working efficiency within an inspection room, plural automatic analyzing apparatuses (hereinafter called analyzing modules) are coupled through a carry thereby to make possible to measure plural items with high processing ability. JP-A-9-243646 discloses an automatic analyzing system in which the same kind of reagent is mounted on at least two of plural analyzing modules, then when the reagent of one of the two analyzing modules becomes shortage, a sample to be analyzed is transferred to the other of the two analyzing modules on which the same kind of reagent is mounted thereby to continue the analysis of the sample without stopping the entirety of the analyzing system for the exchange of the reagent.

SUMMARY OF THE INVENTION

As methods of coping with a case where reagent becomes shortage in an analyzing module, there are two methods as follows. That is, according to one method, the analysis of an analysis item relating to the reagent thus become shortage is hereinafter stopped at the analyzing module (the analyzing module is masked as if the analyzing module could not analyze the analysis item relating to the reagent thus become shortage from the first when viewed from an entire control computer). According to the other method, the analysis of the analyzing module is temporarily stopped, then the reagent thus become shortage is replaced by new one and then the analysis is continued. The reagents are also classified into two kinds as follows. That is, one kind of reagent is frequently used and so when an amount of the reagent becomes shortage, the reagent thus become shortage is preferably replaced by new one at each time of the shortage. In contrast, the other kind of reagent is rarely used and so even when an amount of the reagent becomes shortage, the analysis is desirably continued by another analyzing module on which the same kind of reagent is mounted, whereby the analyzing module having the reagent thus become shortage continues the analysis while masking the reagent thus become shortage in order not to reduce the analyzing efficiency. However, JP-A-9-243646 does not disclose such classification of the two kinds of the reagents. That is, JP-A-9-243646 does not take into consideration as to when an operator exchanges the reagent in the case where the reagent becomes shortage in the analyzing module.

An object of the present invention is to provide an automatic analyzing system which can continue analysis without reducing analyzing efficiency of the entire system even when reagent becomes shortage in an analyzing module.

In order to attain the aforesaid object, according to an aspect of the present invention, in an automatic analyzing system which includes a carry line for carrying a sample rack from a rack sending unit to a rack recovery unit and analyzes samples by using a plurality of analyzing apparatuses which are disposed along the carry line, wherein each of the analyzing apparatuses includes a reaction unit, a sample dispensing unit for dispensing the sample on the sample rack into the reaction unit and a reagent supply unit for supplying reagents corresponding to an analysis item to the reaction unit, the automatic analyzing system including:

a reagent shortage detection unit for detecting that one of the reagents of the reagent supply units of the analyzing apparatuses is shortage;

reagent shortage occurrence display unit which notifies the shortage of the one reagent in response to that the reagent shortage detection unit detects that the one reagent of the analyzing apparatuses is shortage; and control separation unit for separating from the control of the automatic analyzing system, the analyzing apparatus in which the one reagent is shortage, in accordance with reagent shortage detection information from the reagent shortage detection unit.

DETAILED DESCRIPTION OF THE INVENTION

The configuration and operation of the automatic analyzing system according to an embodiment of the present invention will be explained with reference to FIGS. 1 to 5.

First, the entire configuration of the automatic analyzing system according to the embodiment will be explained with reference to FIG. 1.

Figure 1:
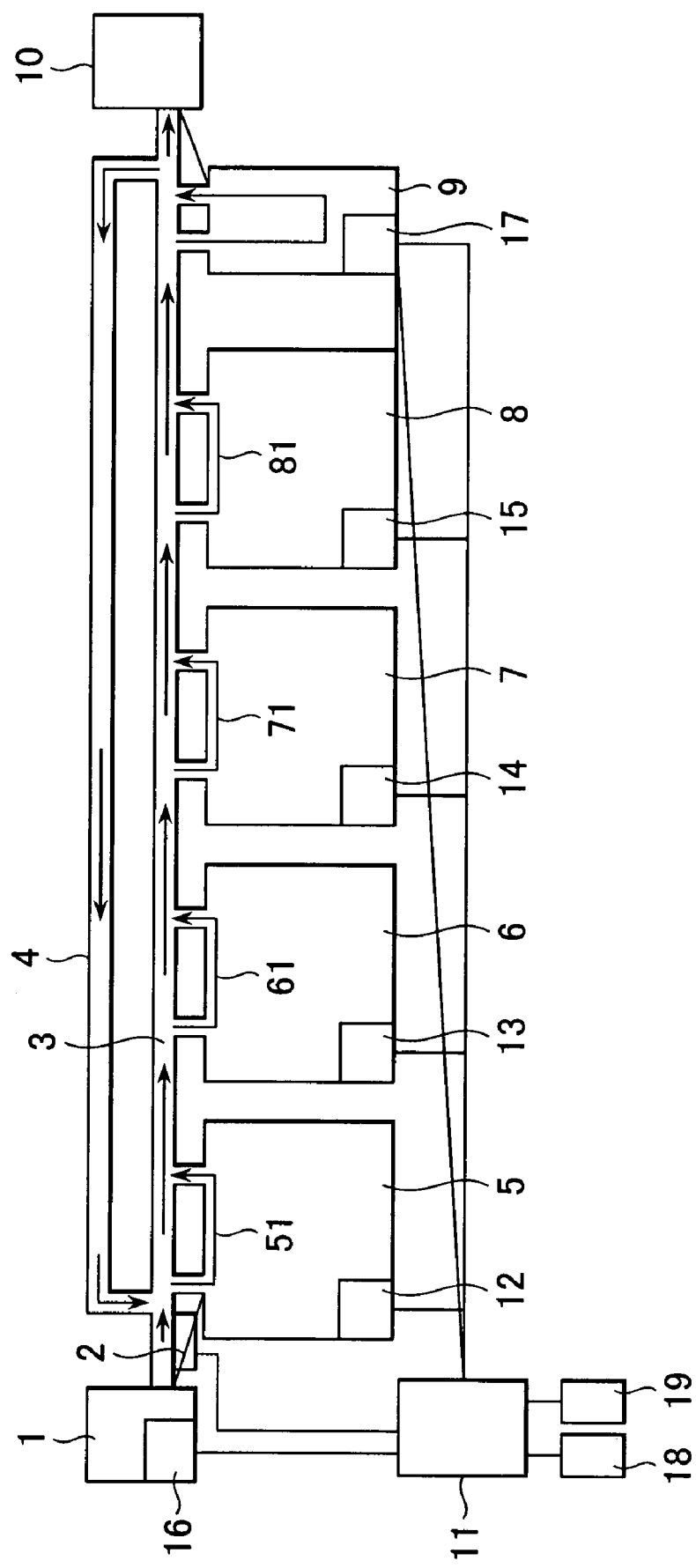
FIG. 1 is a block diagram showing the entire configuration of the automatic analyzing system according to an embodiment of the present invention.

FIG. 1 is a block diagram showing the entire configuration of the automatic analyzing system according to the embodiment of the invention.

The automatic analyzing system according to the embodiment includes a sample rack install unit 1, an ID read unit 2, a carry line 3, a re-inspection carry line 4, analyzing modules 5, 6, 7, 8, a sample rack stand-by unit 9, a sample rack recovery unit 10 and an entire management computer 11.

The sample rack install unit 1 is a portion in which plural sample racks each holding plural samples are installed. The analyzing modules 5, 6, 7 and 8 are disposed along the carry line 3 and are coupled to the carry line 3 so as to be detachable therefrom. The number of the analyzing modules are an arbitrary and this embodiment shows a case where four analyzing modules are used. The four analyzing modules 5, 6, 7 and 8 constitute two analyzing units. That is, a first analyzing unit is constituted by the two analyzing modules on the upstream side of the carry line 3, that is, the analyzing modules 5 and 6, which are set as immunity analyzing modules. A second analyzing unit is constituted by the two analyzing modules on the downstream side of the carry line 3, that is, the analyzing modules 7 and 8, which are set as biochemical analyzing modules. The number of the analyzing modules constituting the biochemical analyzing modules is not limited to two and may be three or more.

Although this embodiment shows a case of the biochemical analyzing modules are combined with the immunity analyzing modules, the embodiment may be constituted by the combination of other analyzing modules such as gene analyzing modules.

The carry line 3 transfers the sample rack installed at the sample rack install unit 1 to a predetermined one of the analyzing modules 5, 6, 7 and 8. The carry line 3 also transfer the sample rack which holds the sample having been analyzed by the analyzing modules 5, 6, 7, 8 so as to be housed within the sample rack recovery unit 10. The analyzing modules 5, 6, 7, 8 have leading lines 51, 61, 71 and 81, respectively. The sample rack is transferred to the analyzing modules 5, 6, 7, 8 from the carry line 3 through the leading lines 51, 61, 71 and 81, respectively. The re-inspection carry line 4 serves to return the sample rack having been analyzed by one of the analyzing modules 5, 6, 7, 8 to the inlet of the carry line 3 when the re-inspection is necessary or when it is necessary to analyze by another of the analyzing modules. The sample rack stand-by unit or buffer 9 is a portion for temporarily waiting the sample having been analyzed by one of the analyzing modules when the sample is to be further analyzed by another of the analyzing modules or for temporarily waiting the sample until the determination result is obtained as to whether or not the re-inspection is to be performed after the completion of the dispensing and analysis has been completed in the analyzing module.

The analyzing modules 5, 6, 7, 8 have computers 12, 13, 14, 15 for performing the control of necessary processings within the analyzing modules, respectively. The sample rack install unit 1 has a computer 16 for performing necessary control within the sample rack install unit 1, the carry line 3, the re-inspection carry line 4 and the sample rack recovery unit 10. Further, the sample rack stand-by unit 9 has a computer 17 for performing necessary control within the sample rack. The computers 12, 13, 14, 15, 16, 17 and the ID read unit 2 are connected to the entire management computer 11. An operation unit 18 for inputting necessary information and a display unit 19 for displaying the analysis result are connected to the entire management computer 11.

The sample held by the sample rack has a sample ID (identifier) representing information (a receipt number, name of a patient, a requested analysis item etc.) relating to the sample. The sample rack has a rack ID representing rack identification information such as a rack number etc. Although the sample rack placed at the sample rack install unit 1 is transferred by the carry line 3, when the sample rack is transferred to the carry line 3, the sample ID and the sample rack ID etc. are read by the ID read unit 2 and sent to the entire management computer 11. The entire management computer 11 determines at which analyzing module the requested analysis item is performed based on the read information and supplies the information to the computer 16 and the one of the computers 12 to 15 corresponding to the analyzing module thus determined.

Figure 2:
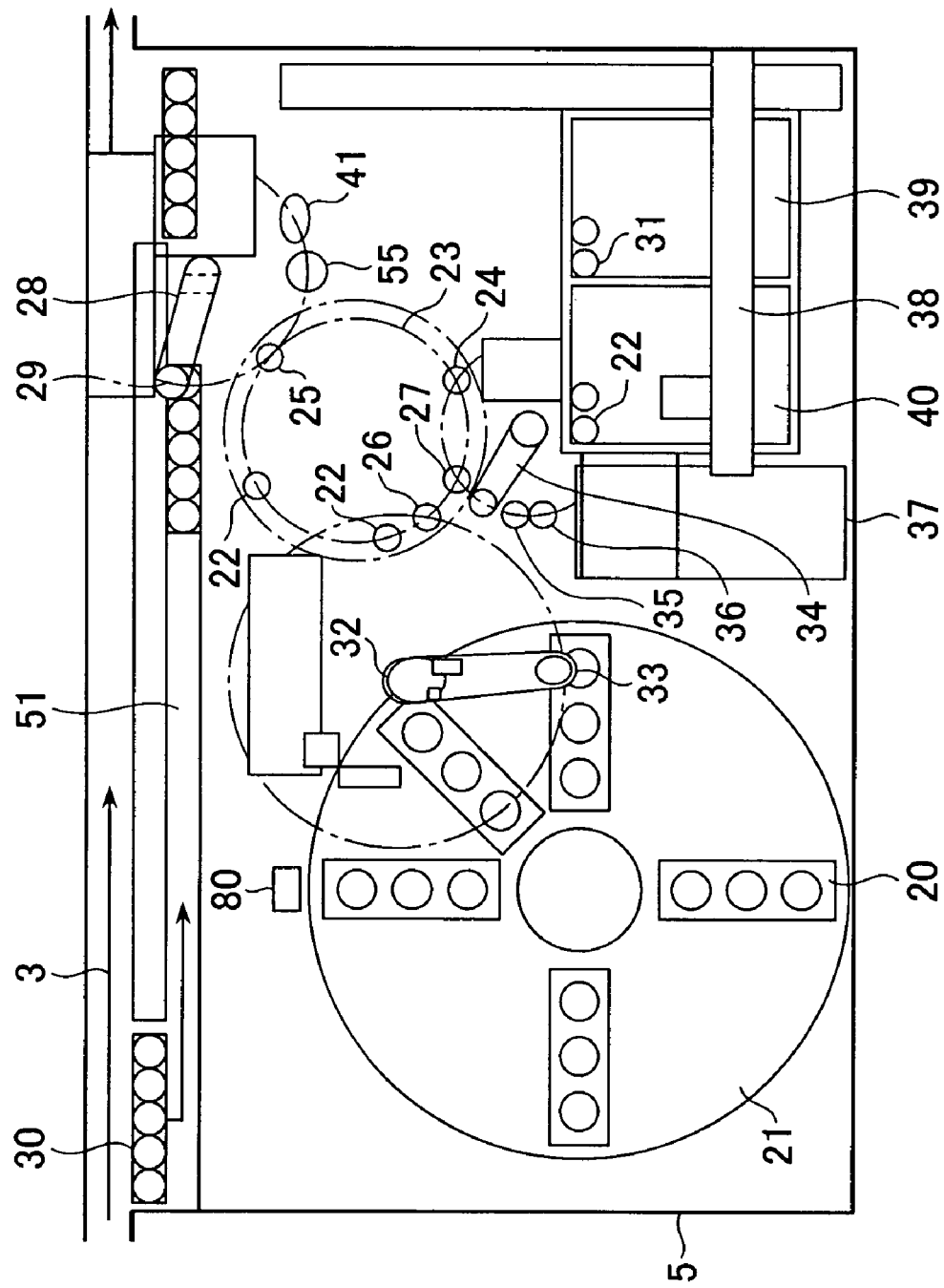
FIG. 2 is a plan view showing the configuration of an immunity analyzing module used in the analyzing system according to the embodiment of the present invention.

Next, the configuration of the immunity analyzing module used in the analyzing system according to the embodiment will be explained with reference to FIG. 2. In FIG. 2, although the explanation is made as to the immunity analyzing module 5 shown in FIG. 1 as an example, the immunity analyzing module 6 has the same configuration. In the figure, portions identical to those of FIG. 1 are referred to by the common symbols, with explanation thereof being omitted.

FIG. 2 is a plan view showing the configuration of the immunity analyzing module used in the analyzing system according to the embodiment of the present invention.

A plurality of reagent containers 20 are disposed on a disc 21 in a circular shape. The entire management computer 11 has a register unit for registering particular reagents. The disc 21 is rotated by a motor. A plurality of reaction containers 22 are disposed on a constant temperature bath 23 in a circular shape. The constant temperature bath 23 is rotated by a motor. In accordance with the rotation of the constant temperature bath 23, each of the reaction containers 22 is moved from a position 24 to a sample dispensing position 25, a reagent dispensing position 26 and a reaction solution suction position 27.

A sample dispensing pipet 28 can be moved to the sample dispensing position 25 from a sample suction position 29 by the motor. In the case of leading a sample rack 30 to the leading line 51 and dispensing the sample held by the sample rack and positioned at the sample suction position 29 into the reaction container 22, a disposable chip 31 is attached to the tip end of the nozzle of the sample dispensing pipet 28.

A reagent dispensing pipet 32 is movable from a reagent suction position 33 to the reagent dispensing position 26. A shipper 34 can be moved among the reaction solution suction position 27, a buffer solution suction position 35 and a flow-cell inside washing position 36. The shipper 34 has a function of sending the reaction solution to the flow cell within a detection unit 37 through a tube.

The chip and a reaction container transfer mechanism 38 transfer the disposable chip 31 to a chip attaching position 55 from a chip storing position 39 and also transfer the reaction container 22 to the reaction container installation position 24 from a reaction container storing position 40. The reagent dispensing pipet 32 and the shipper 34 wash their own nozzles at their washing positions, respectively.

Next, the operation of the immunity analyzing module 5 will be explained.

First, the chip and a reaction container transfer mechanism 38 transfer the disposable chip 31 to the chip attaching position 55 and also transfer the reaction container 22 to the reaction container installation position 24. When the sample is positioned at the sample suction position 29, the disc 21 rotates the reagent container 20, in which the reagent used for analyzing the sample is contained, so as to be positioned at the reagent suction position 33. Further, the sample dispensing pipet 28 is attached at its nozzle with the disposable chip 31, then moved to the sample suction position 29 and sucks the sample. After sucking the sample, the sample dispensing pipet 28 is moved to the sample dispensing position 25 and discharges the sample thus sucked into the reaction container 22. After discharging the sample, the sample dispensing pipet 28 is moved to a chip disposing position 41 and disposes the chip at the tip end thereof.

The reaction container 22 discharged the sample in this manner is moved to the reagent dispensing position 26 through the rotation of the reaction disc 23. The reagent dispensing pipet 32 sucks the reagent disposed at the reagent suction position 33 and discharges the reagent into the reaction container 22 having been moved at the reagent dispensing position 26. Upon the lapse of a predetermined time period, the reaction container 22 in which immunity reaction solution of the reagent and the sample is contained is moved to the reaction solution suction position 27 through the rotation of the reaction disc 23. The shipper 34 sucks the reaction solution, then is moved to the buffer solution suction position 35 thereby to suck the buffer solution and moves these solution to the flow cell within the detection unit 37 through the tube. Thus, the optical measurement is performed thereby to obtain the analysis result of the immunity analysis item. Thereafter, the shipper 34 is moved to the flow-cell inside washing position 36, then sucks the washing solution for washing within the flow cell and flows the solution thus sucked through the tube to wash the flow cell.

Figure 3:
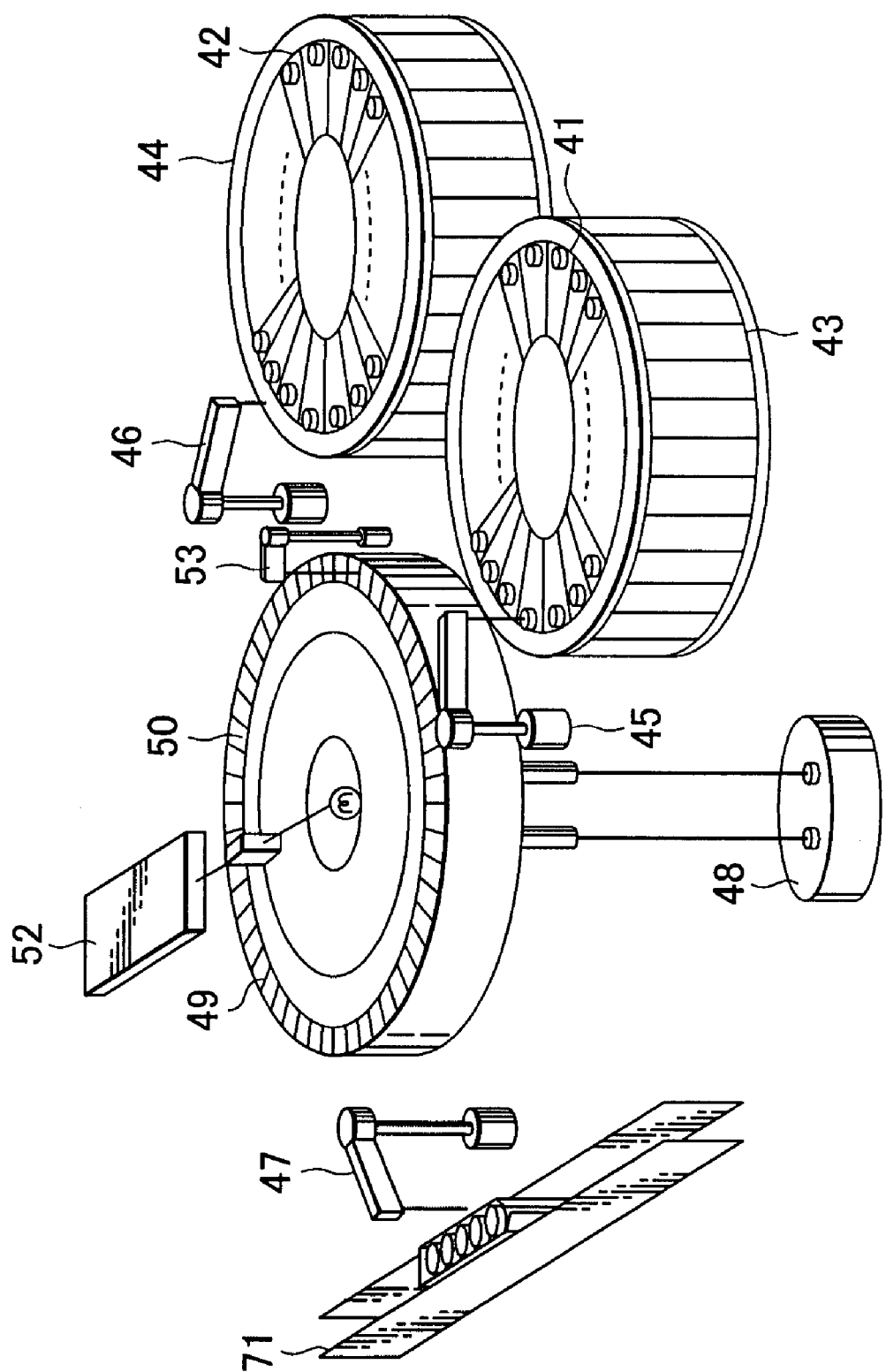
FIG. 3 is a plan view showing the configuration of a biochemical analyzing module used in the analyzing system according to the embodiment of the present invention.

Next, the configuration of the biochemical analyzing module used in the analyzing system according to the embodiment will be explained with reference to FIG. 3. In FIG. 3, although the explanation is made as to the biochemical analyzing module 7 shown in FIG. 1 as an example, the biochemical analyzing module 8 has the same configuration.

In the figure, portions identical to those of FIG. 1 are referred to by the common symbols, with explanation thereof being omitted.

FIG. 3 is a plan view showing the configuration of the biochemical analyzing module used in the analyzing system according to the embodiment of the present invention.

The biochemical analyzing module 7 is provided with a reagent system which includes a first reagent disc 43 on which plural first reagents 41 are disposed in a circular manner, a second reagent disc 44 on which plural second reagents 42 are disposed in a circular manner and first and second reagent dispensing pipets 45, 46; a sample system having a sample dispensing pipet 47; a reaction system having plural reaction containers 50 disposed on a reaction disc 49 in which constant temperature liquid from a constant temperature bath 48 circulates; and a measurement system (analysis system) having a multi-wave photometer 52.

The sample rack 30 holding the sample is led into a leading line 71, and so the sample positioned at the sample sucking position is sucked by the sample dispensing pipet 47 and discharged into the reaction container 50 of the reaction disc 49 at a sample dispensing position. The reaction container 50 in which the sample was discharged is moved to a first reagent dispensing position. At the first reagent dispensing position, the first reagent 41 held by the first reagent disc 43 is dispensed into the reaction container 50 by the reagent dispensing pipet 45. The reaction container 50 in which the first reagent was dispensed is moved to a stirring position. At the stirring position, a stirring device 53 stirs the sample and the first reagent within the reaction container 50.

Further, when it is necessary to add the second reagent, the reaction container 50 having been subjected to the stirring process is moved to a second reagent dispensing position. At the second reagent dispensing position, the second reagent 42 held by the second reagent disc 44 is dispensed into the reaction container 50 by the reagent dispensing pipet 46. The reaction container 50 in which the second reagent was dispensed is moved to a stirring position. At the stirring position, the stirring device 53 stirs the sample, the first reagent 'A'nd the second reagent within the reaction container 50 to generate reaction solution.

The reaction container 50 in which the reaction solution is contained is moved to a measurement position. At the measurement position, the multi-wave photometer 52 measures the multi-wave absorbance of the reaction solution to obtain the analysis result of the biochemical analysis item.

Next, the explanation will be made with reference to FIG. 4 as to the processing operation for making it possible to exchange reagent when an amount of the reagent becomes shortage in the automatic analyzing system according to the embodiment of the present invention. That is, for example, the explanation will be made as to the exchange of reagent in the case where, during the execution of the automatic analyzing processing in the automatic analyzing system according to the embodiment, the remaining amount of a particular reagent of the analyzing module 5 becomes shortage and so it becomes impossible to continue the measurement of the reagent. In each of the other analyzing modules 6, 7 and 8, the exchange of reagent is performed in the same manner in the case where the remaining amount of a reagent of the analyzing module becomes shortage and so it becomes impossible to continue the measurement of the reagent.

Figure 4:
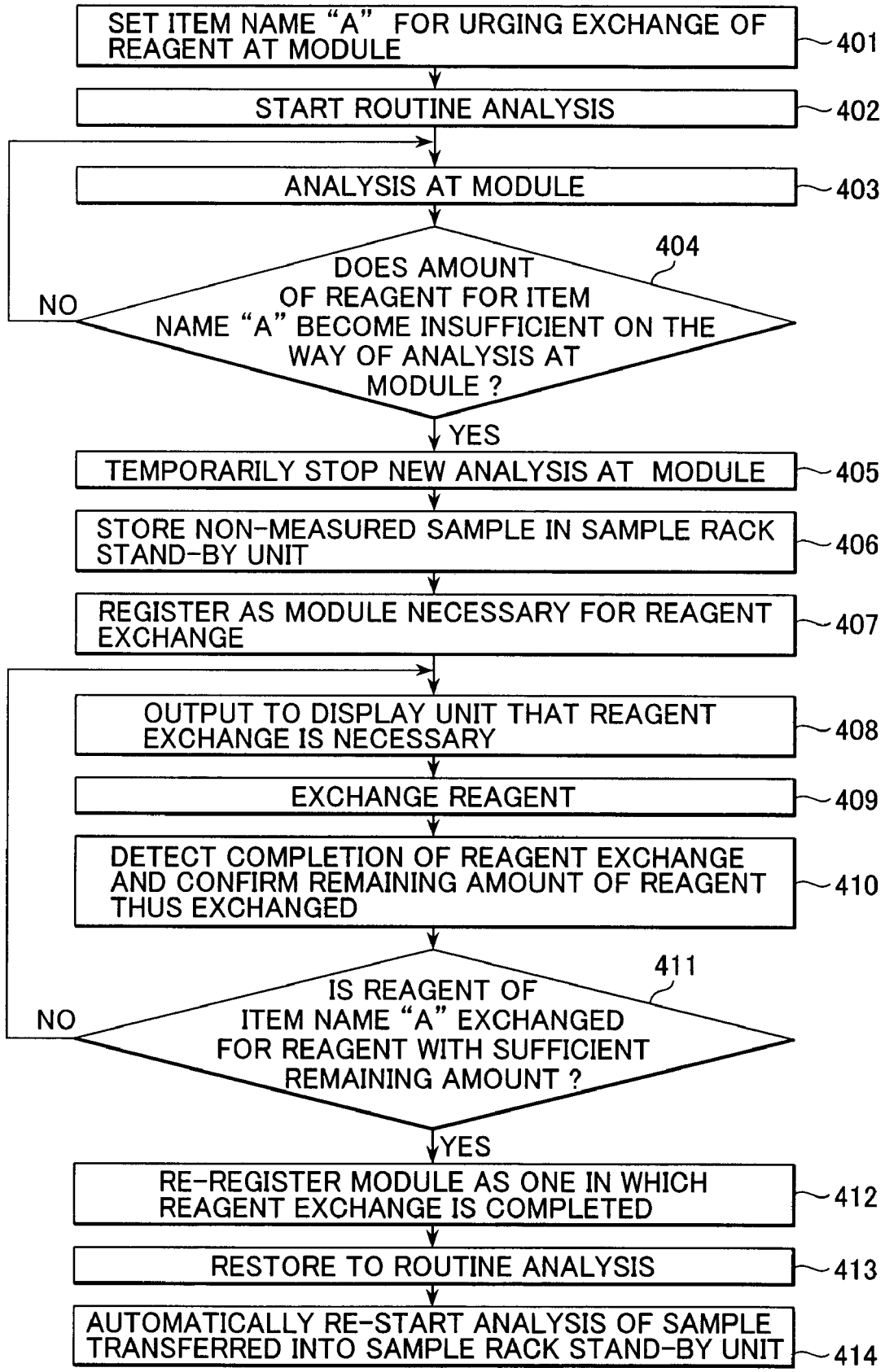
FIG. 4 is a flow chart showing the procedure of the system operation in the automatic analyzing system according to the embodiment of the present invention.

FIG. 4 is a flow chart showing the processing operation in the case where the remaining amount of a particular reagent in the automatic analyzing system according to the embodiment of the present invention becomes shortage and so it becomes impossible to continue the measurement of the reagent.

Figure 5:
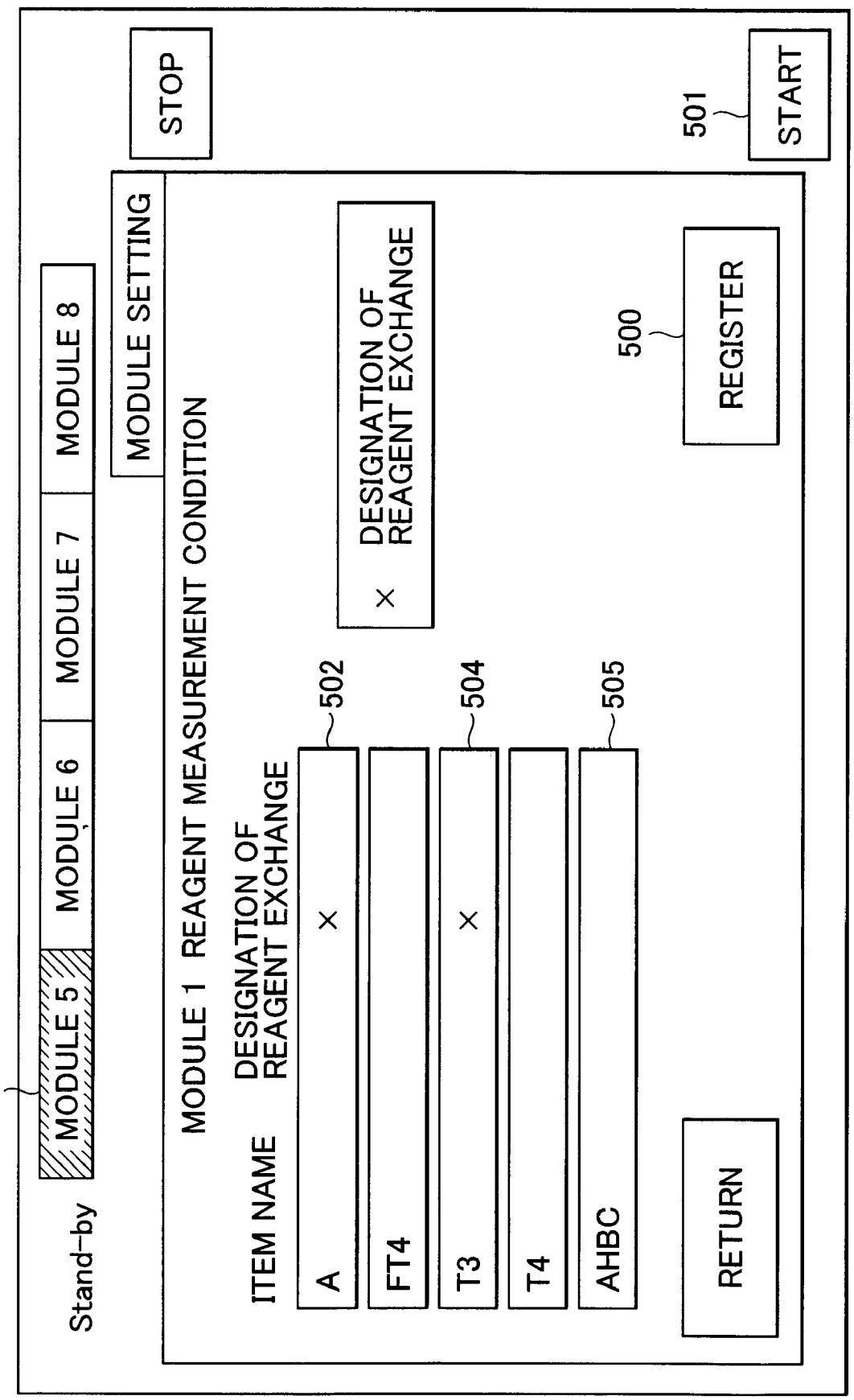
FIG. 5 is an explanatory diagram showing an example of setting reagent exchange items in the analyzing module according to the embodiment of the present invention.

FIG. 5 is an explanatory diagram showing an example of setting the reagent exchange item at the operation unit 18 of the analyzing module according to the embodiment of the present invention.

In step 401, an item name of measurement for urging the exchange of the reagent is designated for the analyzing module, and a register button 500 is pushed thereby to set the reagent of the item name 'A' (502) as being designated.

In step 402, when a analysis start button 501 is selected, the entire management computer 11 of the automatic analyzing system executes the usual routine analysis.

Then, in step 403, each of the module computers 12 to 15 executes the analysis.

In step 404, the module computer 12 determines whether or not an amount of the reagent for the item name 'A' becomes insufficient on the way of the analysis. When it is determined that the reagent does not become insufficient, the process returns to step 403 to continue the analysis at the module. In contrast, when it is determined that the reagent becomes insufficient, the process proceeds to step 405. The following explanation will be made as to the case where the reagent for the item name 'A' become insufficient. The same operation will be made as to the case where the reagent for an item name 504 which is designated to be exchanged becomes insufficient. In contrast, when the reagent for an item name 505 which is not designated to be exchanged becomes insufficient, the analysis at the module is continued in step 403 and all the item names except for the item name 505 are analyzed.

In step 405, the module computer 12 temporarily stops the analysis of a new sample at the module and continuously measures the item relating to the sample having been sucked already. Then, in step 406, the samples having not been measured yet due to the temporal stop of the analysis are transferred to the sample rack stand-by unit 9.

In step 407, the entire management computer 11 of the automatic analyzing system registers the analyzing module 5 as an analyzing module necessary for exchange the reagent. Then, in step 408, it is displayed on the display unit 19 that the exchange of the reagent 'A' is necessary. The following explanation will be made as to the case where the reagent becomes shortage at the analyzing module 5. The display showing a state that the exchange of the reagent is necessary is made on the display unit 19 coupled to the entire management computer 11, for example. The display unit 19 schematically displays the analyzing modules 5, - - -, 8 etc. For example, when the reagent is required to be exchanged at the analyzing module 5, the display 503 of the analyzing module 5 is changed into a blinking state of "pink" form a normally lightened state of "green".

In step 409, the exchange of the reagent 'A't the analyzing module 5 is made possible. During the execution of the operation of step 409, the entire management computer 11 instructs the routine analysis to the analyzing modules 6 - - -, 8 thereby to continue the analysis.

In step 410, the module computer 12 detects the completion of the exchange of the reagent in response to a signal from a detector 80 attached to the analyzing module 5 and confirms the remaining amount of the reagent thus exchanged based on a signal from a liquid surface detection sensor attached to the reagent dispensing pipet 32.

In step 411, the entire management computer 11 determines whether or not the remaining amount of the reagent for the item name 'A' is sufficient. When it is determined that the remaining amount is still shortage, the process returns to step 408 and it is displayed on the display unit 19 that the exchange of the reagent 'A' is necessary thereby to urge the exchange of the reagent 'A' again. In contrast, when the reagent is exchanged and there is sufficient remaining amount, the process proceeds to step 412.

In step 412, the entire management computer 11 registers the analyzing module 5 again as an analyzing module which has completed the exchange of the reagent.

In step 413, the entire management computer 11 restores the analyzing module 5 to the automatic analyzing system as an analyzing module of the routine.

Further, in step 414, the sample having been transferred to the sample rack stand-by unit 9 is moved to the analyzing module 5 and the measurement of this sample having been stopped is automatically re-started.

Although the explanation is made as to the case where a reagent for the item name 'A' becomes shortage, a reagent etc. necessary for analyzing the item name 'A' is not limited to one. That is, the aforesaid embodiment can also be applied when washing solution, dilution solution or pre-processing solution becomes shortage. To be more concrete, even when the remaining amount of the reagent for the item name 'A' is sufficient, when the remaining amount of one of the washing solution, the dilution solution and the pre-processing solution becomes shortage, the module computer 12 determines in step 404 that the remaining amount of one of the washing solution, the dilution solution and the pre-processing solution is shortage and so the process may proceed to step 405.

As explained above, according to the embodiment, even when the remaining amount of a reagent to be analyzed becomes shortage at one of the plural analyzing modules, the reagent can be exchanged and continue the analysis without stopping the entire operation of the analyzing system.

Accordingly, the present invention can provide the analyzing system which can continue the analysis without reducing the analyzing efficiency of the entire system even when the remaining amount of a reagent becomes shortage at the analyzing module.

What is claimed is:

1. An automatic analyzing system which analyzes samples, the automatic analyzing system comprising:
   a carry line;
   a plurality of analyzing apparatuses, each containing a corresponding reagent, which are disposed along the carry line;
   a reagent shortage detection unit for detecting that the corresponding reagent used in analyzing a sample in any of the analyzing apparatuses is short; and
   a management computer for controlling operations of said analyzing system, said management computer including a register unit to register particular reagents in the analyzing system, and the management computer being configured to register any of the analyzing apparatuses in which any one of said particular reagents is detected as being short; and
   a plurality of module computers for the plurality of analyzing apparatuses, the plurality of module computers each corresponding to one of the plurality of analyzing apparatuses, each module computer being programmed to stop the corresponding analyzing apparatus in which any one of said particular reagents registered is detected as being short.

2. An automatic analyzing system according to claim 1 wherein each module computer is further programmed to continue operation of the corresponding analyzing apparatus when the corresponding reagent has not become insufficient.

3. An automatic analyzing system according to claim 1, further comprising
   a stand-by unit wherein when any one of the analyzing apparatuses is stopped in order to replace the corresponding reagent, the stand-by unit places the sample in said one of the analyzing apparatuses in a stand by state, and the module computers corresponding to other analyzing apparatuses which are not stopped are programmed so as not to stop the analysis of the entire system during a time period where the corresponding reagent to be replaced is supplied to said one of the analyzing apparatuses which is stopped.

4. An automatic analyzing system according to claim 1, further comprising a detector and wherein
   when any one of the analyzing apparatuses is stopped, the corresponding module computer corresponding to said one of the analyzing apparatuses which is stopped is programmed such that, when receiving a signal from the detector indicating that completion of replacing the corresponding reagent in said one of the analyzing apparatuses which is stopped, confirms a remaining amount of the corresponding reagent replaced in said one of the analyzing apparatuses which is stopped before said one of the analyzing apparatuses is restored to operation.

5. An automatic analyzing system according to claim 1, wherein, when any one of the analyzing apparatuses is stopped, the corresponding module computer corresponding to said one of the analyzing apparatuses which is stopped is programmed to confirm automatically, before said one of the analyzing apparatuses which is stopped is restored to operation, whether or not a reagent replaced in said one of the analyzing apparatuses which is stopped coincides with an item for measurement relating to the corresponding reagent detected to be short for said one of the analyzing apparatuses which is stopped, wherein when the reagent replaced does not coincide with the item, said one of the analyzing apparatuses which is stopped is not restored to operation.

6. An automatic analyzing system according to claim 1, wherein, when any one reagent in any one of the analyzing apparatuses is detected as being short, the corresponding module computer corresponding to said one of the analyzing apparatuses is programmed to determine a reagent to be exchanged based on an identifier of the one reagent detected to be short and said one of the analyzing apparatuses in which the one reagent is detected to be short is automatically stopped.

7. An automatic analyzing system according to claim 6, wherein, when any one reagent in any one of the analyzing apparatuses is detected as being short, the corresponding module computer corresponding to said one of the analyzing apparatuses is programmed to identify the one reagent to be exchanged by automatically confirming, based on the identifier of the one reagent detected to be short.

* * * * *